(12) United States Patent  
Rakshit

(10) Patent No.: US 11,195,490 B1  
(45) Date of Patent: Dec. 7, 2021

(54) SMART CONTACT LENS WITH ADJUSTABLE LIGHT TRANSMITTANCE

(71) Applicant: INTERNATIONAL BUSINESS MACHINES CORPORATION, Armonk, NY (US)

(72) Inventor: Sarbajit K. Rakshit, Kolkata (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/887,371

(22) Filed: May 29, 2020

(51) Int. Cl.
| | |
|---|---|
| G09G 3/38 | (2006.01) |
| G16Y 20/40 | (2020.01) |
| G06F 3/01 | (2006.01) |
| G02C 7/04 | (2006.01) |
| G02C 7/10 | (2006.01) |
| A61B 3/11 | (2006.01) |
| H04W 88/02 | (2009.01) |

(52) U.S. Cl.
CPC ............... *G09G 3/38* (2013.01); *A61B 3/112* (2013.01); *G02C 7/04* (2013.01); *G02C 7/101* (2013.01); *G06F 3/015* (2013.01); *G16Y 20/40* (2020.01); *H04W 88/02* (2013.01)

(58) Field of Classification Search
CPC .............. G09G 3/38; G02C 7/04; G06F 3/015
USPC ................................................ 345/7, 8, 173
See application file for complete search history.

(56) References Cited

U.S. PATENT DOCUMENTS

| | | | |
|---|---|---|---|
| 10,353,463 | B2 | 7/2019 | Shtukater |
| 2014/0320799 | A1 | 10/2014 | Pugh et al. |
| 2015/0234205 | A1 | 8/2015 | Schowengerdt |
| 2015/0362756 | A1 | 12/2015 | Wiser et al. |
| 2016/0299354 | A1* | 10/2016 | Shtukater ................. G02C 7/04 |
| 2017/0023793 | A1 | 1/2017 | Shtukater |
| 2017/0235931 | A1* | 8/2017 | Publicover .......... H04L 63/0861 |
| 2017/0357107 | A1* | 12/2017 | Rousseau ............... G02C 7/101 |
| 2017/0364732 | A1* | 12/2017 | Komogortsev .... G06K 9/00604 |
| 2019/0332168 | A1 | 10/2019 | Weldemariam et al. |
| 2020/0004023 | A1* | 1/2020 | Shin ..................... G02B 6/0016 |

FOREIGN PATENT DOCUMENTS

AU            2017202009              4/2017

OTHER PUBLICATIONS

Wikipedia, "Pupillary light reflex", downloaded Apr. 11, 2020, 8 pages.
Wikipedia, "microLED", downloaded Apr. 11, 2020, 9 pages.
Anonymous, "AR contact lenses place micro-displays inside your eyes", downloaded Apr. 11, 2020, 11 pages.

(Continued)

*Primary Examiner* — Calvin C Ma
(74) *Attorney, Agent, or Firm* — Brian Restauro; Andrew D. Wright; Roberts Calderon Safran & Cole, P.C.

(57) ABSTRACT

A method includes: determining, by a computing device, historic eye data of a user; determining, by the computing device, a current eye condition of the user based on: current data from a photodiode sensor of a smart contact lens worn by the user; current data from an image sensor of the smart contact lens worn by the user; and the historic eye data of the user; and adjusting, by the computing device, a transmittance of the smart contact lens worn by the user based on the determined current eye condition.

20 Claims, 7 Drawing Sheets

(56) References Cited

OTHER PUBLICATIONS

Vincent, "LG's latest ridiculous OLED screen is transparent, flexible, and taller than Tom Cruise", Jun. 22, 2017, The Verge, 3 pages.
Waltz, "Smart Contact Lens Doubles as Blood-Sugar Monitor", Jan. 24, 2018, IEEE Spectrum, 3 pages.
Papas, "Contact lens technology to 2020 and beyond: a review of recent patent literature", Sep. 3, 2017, Wiley Online Library, 25 pages.
Bolton, "Samsung Patents Design for 'Smart' Augmented Reality Contact Lenses", Apr. 6, 2016, Independent, 7 pages.
Gupton et al., "What's the Difference Between AR, VR. and MR?" Jan. 6, 2020, The Franklin Institute, 2 pages.
Kim et al., "Next generation smart window display using transparent organic display and light blocking screen", Apr. 2, 2018, vol. 26, No. 7, 10 pages.
Welch, "Panasonic's transparent display is hard for your eyes to believe", Jan. 7, 2016, The Verge, 6 pages.
Anonymous, "How Do I See Depth", downloaded May 29, 2020, 2 pages.
Sayej, "Meet the people using VR, AR, and smart contact lenses to help the blind see", Apr. 19, 2018, Wareable, 5 pages.

\* cited by examiner

SMART CONTACT LENS WITH ADJUSTABLE LIGHT TRANSMITTANCE

BACKGROUND

Aspects of the present invention relate generally to smart contact lenses and, more particularly, to smart contact lenses that can be used to aid a user experiencing eye strain and that can be used to display virtual reality content to a user.

Smart contact lenses are lenses worn on the eye of a user, where the lenses include circuitry to perform one or more computing tasks.

SUMMARY

In a first aspect of the invention, there is a computer-implemented method including: A method, comprising: determining, by a computing device, historic eye data of a user; determining, by the computing device, a current eye condition of the user based on: current data from a photo-diode sensor of a smart contact lens worn by the user; current data from an image sensor of the smart contact lens worn by the user; and the historic eye data of the user; and adjusting, by the computing device, a transmittance of the smart contact lens worn by the user based on the determined current eye condition.

In another aspect of the invention, there is a computer program product including one or more computer readable storage media having program instructions collectively stored on the one or more computer readable storage media. The program instructions are executable to: adjust a transmittance of an electrochromic layer of a smart contact lens based on data from one or more light sensors that are external to a user wearing the smart contact lens In another aspect of the invention, there is a system, comprising a smart contact lens that includes: an electrochromic layer; a display layer; and a control circuit configured to adjust a transmittance of the electrochromic layer to a predefined value while concurrently controlling the display layer to display virtual reality content to a user wearing the smart contact lens.

BRIEF DESCRIPTION OF THE DRAWINGS

Aspects of the present invention are described in the detailed description which follows, in reference to the noted plurality of drawings by way of non-limiting examples of exemplary embodiments of the present invention.

DETAILED DESCRIPTION

Figure 1:
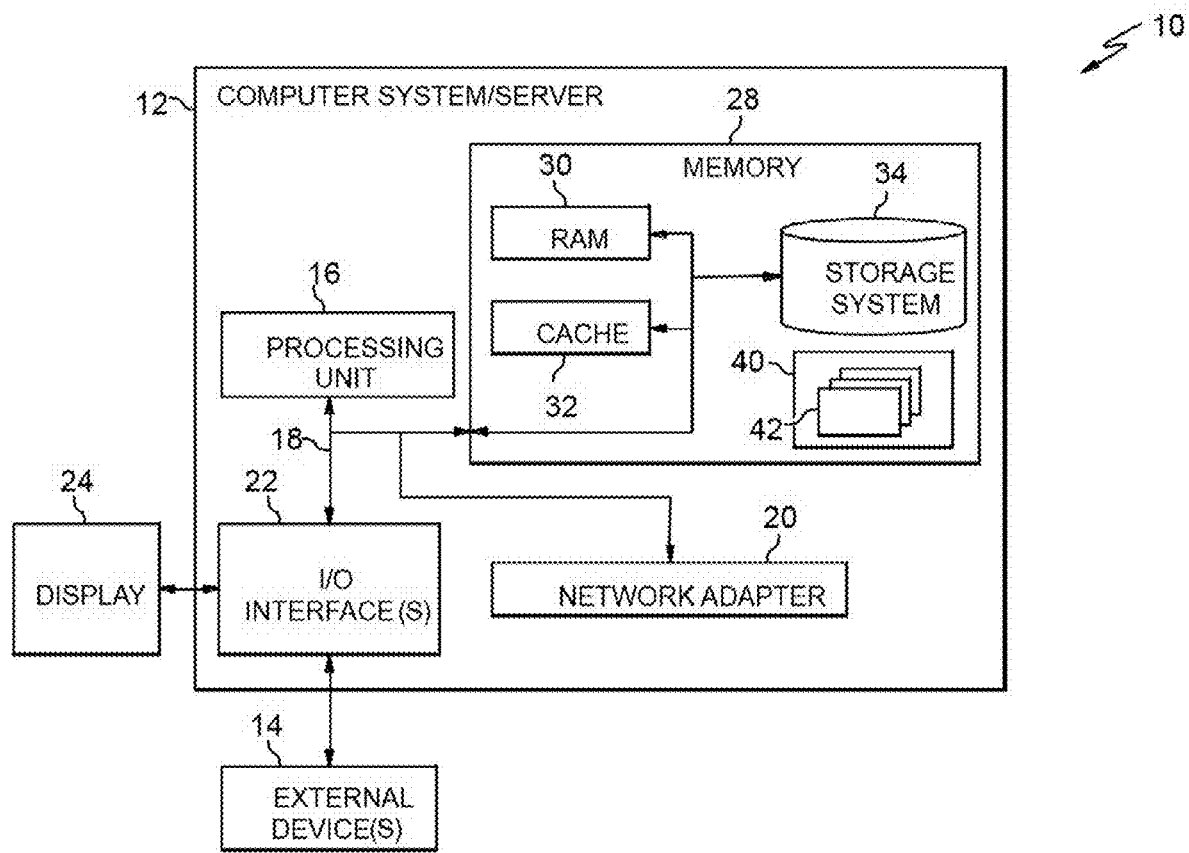
FIG. 1 depicts a computer infrastructure according to an embodiment of the present invention.

Aspects of the present invention relate generally to smart contact lenses and, more particularly, to smart contact lenses that can be used to aid a user experiencing eye strain and that can be used to display virtual reality content to a user. According to aspects of the invention, a smart contact lens includes a layer whose transmittance can be adjusted, so that the lens controls an amount of light that reaches the user's eye. In one embodiment, the lens adjusts the transmittance reactively in response to a determined eye condition. In another embodiment, the lens adjusts the transmittance proactively in response to a predicted abrupt light change. In another embodiment, the lens adjusts the transmittance to be opaque concurrently with displaying virtual reality contact on a display layer of the lens.

The pupillary light reflex (PLR) is a reflex that controls the diameter of the pupil, in response to the intensity (luminance) of light that falls on the retinal ganglion cells of the retina in the back of the eye, thereby assisting in adaptation of vision to various levels of lightness/darkness. A greater intensity of light causes the pupil to constrict (miosis/myosis; thereby allowing less light in), whereas a lower intensity of light causes the pupil to dilate (mydriasis, expansion; thereby allowing more light in). Thus, the pupillary light reflex regulates the intensity of light entering the eye. Some users experience eye strain due to a relatively slow pupillary light reflex. Aspects of the invention address this issue by providing a smart contact lens that includes a layer that has an adjustable transmittance that is actively controlled to regulate an amount of light that passes through the lens and falls on the eye.

Smart contact lens does not have virtual reality (VR) capability. Some smart contact lenses have augmented reality (AR) capability. However, VR differs from AR. In particular, AR adds computer generated visual elements to a live (e.g., real world) view. AR is most typically achieved by the user looking through a transparent screen to obtain the live view, while the computer device displays visual elements on the transparent screen such that the visual elements are superimposed on the user's live view. VR differs from AR in that VR does not use a live view. Instead, in VR, the user's vision is completely immersed in a computer-generated view. VR systems involve large headsets and/or glasses that block the entirety of the user's live view.

Implementations of the invention address this shortcoming by adjusting the transmittance of the electrochromic layer to be opaque, such that the smart contact lens blocks the entirety of the user's live view. In this manner, implementations of the invention provide a VR system for smart contact lenses by adjusting a transmittance of an electrochromic layer to be opaque while concurrently controlling a display layer to display virtual reality content to a user wearing the smart contact lens.

It should be understood that, to the extent implementations of the invention collect, store, or employ personal information provided by, or obtained from, individuals (for example, image data of a user's eye) such information shall be used in accordance with all applicable laws concerning protection of personal information. Additionally, the collection, storage, and use of such information may be subject to consent of the individual to such activity, for example, through "opt-in" or "opt-out" processes as may be appropriate for the situation and type of information. Storage and use of personal information may be in an appropriately secure manner reflective of the type of information, for example, through various encryption and anonymization techniques for particularly sensitive information.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium or media, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Referring now to FIG. 1, a schematic of an example of a computer infrastructure is shown. Computer infrastructure 10 is only one example of a suitable computer infrastructure and is not intended to suggest any limitation as to the scope of use or functionality of embodiments of the invention described herein. Regardless, computer infrastructure 10 is capable of being implemented and/or performing any of the functionality set forth hereinabove.

In computer infrastructure 10 there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system executable instructions, such as program modules, being executed by a computer system. Generally, program modules may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system 12 in computer infrastructure 10 is shown in the form of a general-purpose computing device. The components of computer system 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc.

Figure 2:
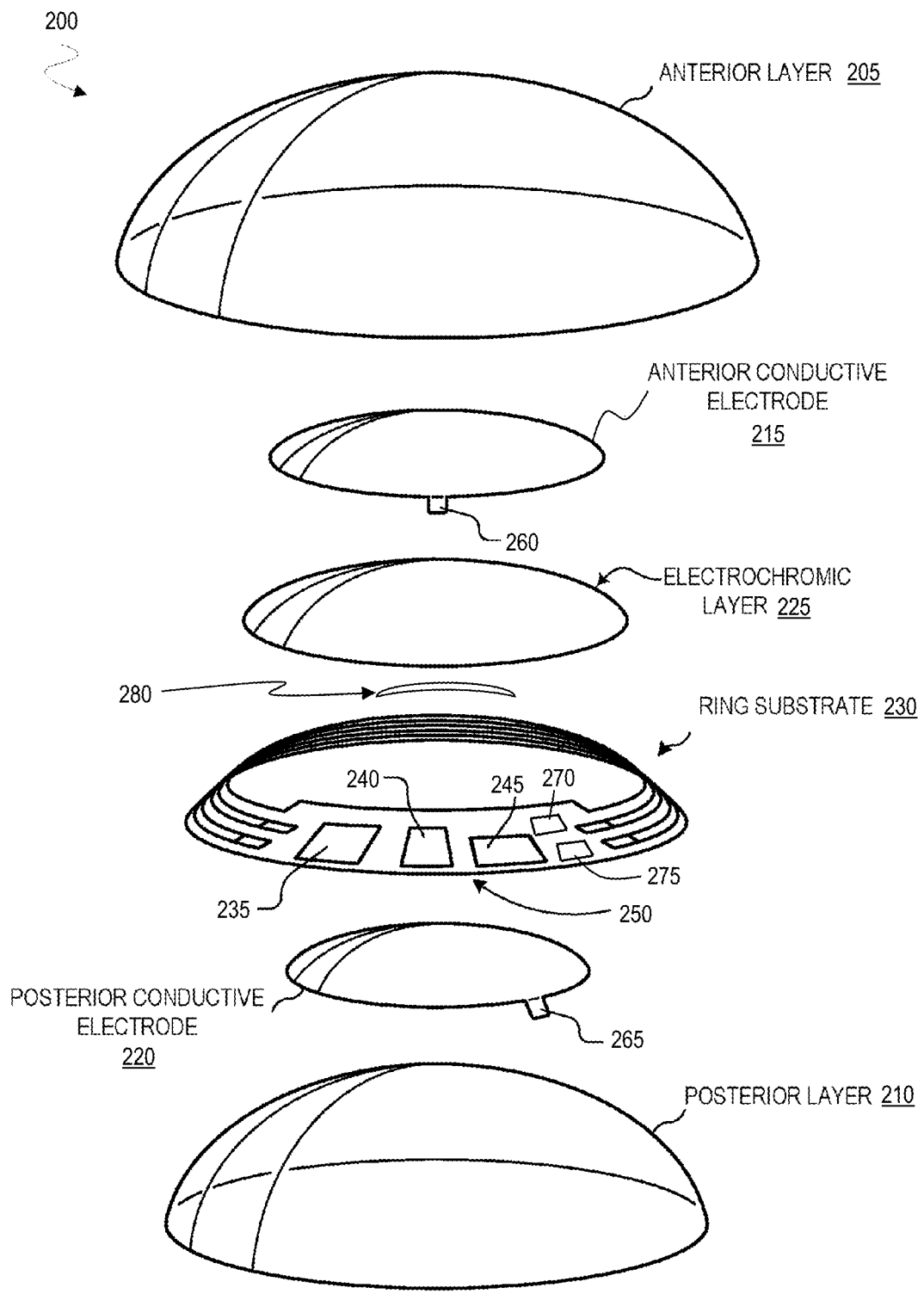
FIG. 2 shows a diagram of an exemplary lens in accordance with aspects of the invention.

FIG. 2 is an exploded perspective view illustrating an embodiment of a smart contact lens 200 in accordance with aspects of the invention. The illustrated embodiment of the smart contact lens 200 includes a flexible lens enclosure including an anterior layer 205, a posterior layer 210, an anterior conductive electrode 215, a posterior electrode 220, an electrochromic layer 225, a ring substrate 230, a power supply 235, a control circuit 240, an anterior contact pad 245, a posterior contact pad 250 (hidden in FIG. 2), a photodiode sensor 270, an image sensor 275, and a display layer 280.

Anterior layer 205 and posterior layer 210 can be formed using molds that are spray coated or injected with a flexible, transparent material. The flexible, transparent material that can be used include any of a polymeric material, a hydrogel, PMMA, silicone based polymers (e.g., fluoro-silicon acrylate), or otherwise.

In embodiments, the ring substrate 230, including power supply 235, control circuit 240, photodiode sensor 270, and image sensor 275, is positioned between the anterior layer 205 and the posterior layer 210 including positioning the substrate over the convex surface of posterior layer 210. In embodiments, the power supply 235 comprises a rechargeable battery. The photodiode sensor 270 is a device (e.g., a semiconductor device) that converts light into an electrical current. In embodiments, the photodiode sensor 270 is electrically connected to the power supply 235 (e.g., via the ring substrate 230) in a manner such that the current that is output by the photodiode sensor 270 is used to charge the rechargeable battery of the power supply 235. In embodiments, the output of the photodiode sensor 270 is proportional to an amount of ambient light that is incident on the photodiode sensor 270, and this output is provided to and used by the control circuit 240 (e.g., via the ring substrate 230) to indicate an amount of ambient light that is incident on the smart contact lens 200. In embodiments, the ring substrate 230 and/or the control circuit 240 comprise one or more antenna elements that are configured to provide wireless communication between the smart contact lens 200 and a computer device, such as a mobile device of a wearer of the smart contact lens 200, e.g., as shown in and described with respect to FIG. 4. In this manner, the computer device may provide control signals and other information to the smart contact lens 200.

The electrochromic layer 225 is composed of a material that changes its transmittance based on an amount of voltage that is applied to the material. The electrochromic layer 225 used in implementations of the invention may comprise any conventional or later-developed electrochromic material including but not limited to: metal oxides (e.g., tungsten oxide), polymers (e.g., polypyrrole, PEDOT, and polyaniline), and suitable organics.

According to aspects of the invention, the anterior conductive electrode 215, the electrochromic layer 225, and the posterior conductive electrode 220 form an electrochromic element, the transmittance of which is selectively controlled by the control circuit 240 by applying a voltage to the electrochromic layer 225 via the power supply 235. In embodiments, the anterior conductive electrode 215 and the posterior conductive electrode 220 are transparent electrodes that electrically manipulate the electrochromic layer 225 via the application of a voltage and/or current across the electrodes. The anterior conductive electrode 215 and the posterior conductive electrode 220 are flexible conductors that substantially maintain their conductivity even in the presence of cyclical mechanical stress including folding and bending. The anterior conductive electrode 215 and the posterior conductive electrode 220 can be formed from an optically transparent but electrically conductive material that is cured onto, and therefore conforms to, the curved surfaces of the anterior layer 205 and the posterior layer 210, respectively. The illustrated embodiment of the anterior conductive electrode 215 includes a connection tab 260 and the illustrated embodiment of the posterior conductive electrode 220 includes a connection tab 265. The tabs 260 and 265 are used to provide electrical connection between the electrodes in the ring substrate 230 (i.e., respectively contacting the anterior contact pad 245 and the posterior contact pad 250). They can be radially offset from each other in one embodiment, or circumferentially offset in other embodiments.

With continued reference to FIG. 2, in accordance with aspects of the invention, the smart contact lens 200 includes an image sensor 275 that is configured to obtain real-time images of an interior of the eye of a user that is wearing the smart contact lens 200. In embodiments, the system uses data obtained by the image sensor 275 to selectively adjust the transmittance of the electrochromic layer 225, as described herein. In an exemplary embodiment, the image sensor 275 comprises an inward facing camera, where inward facing in this context refers to a direction toward the interior of the eye of the wearer of the smart contact lens 200. In another exemplary embodiment, the image sensor 275 comprises an inward facing image capture sensor optionally coupled with the rear facing emitter of an invisible light, for example infrared (IR) emitter. In either embodiment, the image sensor 275 is configured to obtain image data of the eye that the system uses to identify and track changes in position of the pupil of the eye of the user wearing the smart contact lens 200. In particular, the system uses image data obtained by the image sensor 275 (e.g., size of the pupil, position of portions of the pupil, etc.) to determine a diameter of the pupil in real time, and uses determined diameters of the pupil over time (e.g., changes in diameter) as a measure of the pupillary light reflex (PLR) or photopupillary reflex of the user wearing the smart contact lens 200.

Still referring to FIG. 2, and in accordance with aspects of the invention, the smart contact lens 200 includes a display layer 280 that is configured to display visual content to a wearer of the smart contact lens 200. In embodiments, the display layer 280 comprises a micro display, such as a high resolution microLED display, for example. In a particular exemplary embodiment, the display 200 comprises a 14 k pixels-per-inch micro-display. In embodiments, the display layer 280 is operatively connected to the control circuit 240 by a portion of the ring substrate 230, such that the control circuit 240 provides control signals to the display to cause the display layer 280 to show content defined by the control signals (e.g., by selectively energizing individual pixels of the display layer 280). In this manner, the display layer 280 is controlled to display visual content (e.g., text, shapes, colors, pictures, video, etc.) to a user wearing the smart contact lens 200.

According to aspects of the invention, the display layer 280 is located on a side of the electrochromic layer 225 that is closer to the user's eye when the user is wearing the smart contact lens 200. In this manner, the display layer 280 is located between the user's eye and the electrochromic layer 225 when the user is wearing the smart contact lens 200. As a result of this configuration, the system may control the electrochromic layer 225 to be completely opaque (e.g., 0% transmittance) concurrently with controlling the display layer 280 to display content to the eye of the user, as described herein.

Figure 3:
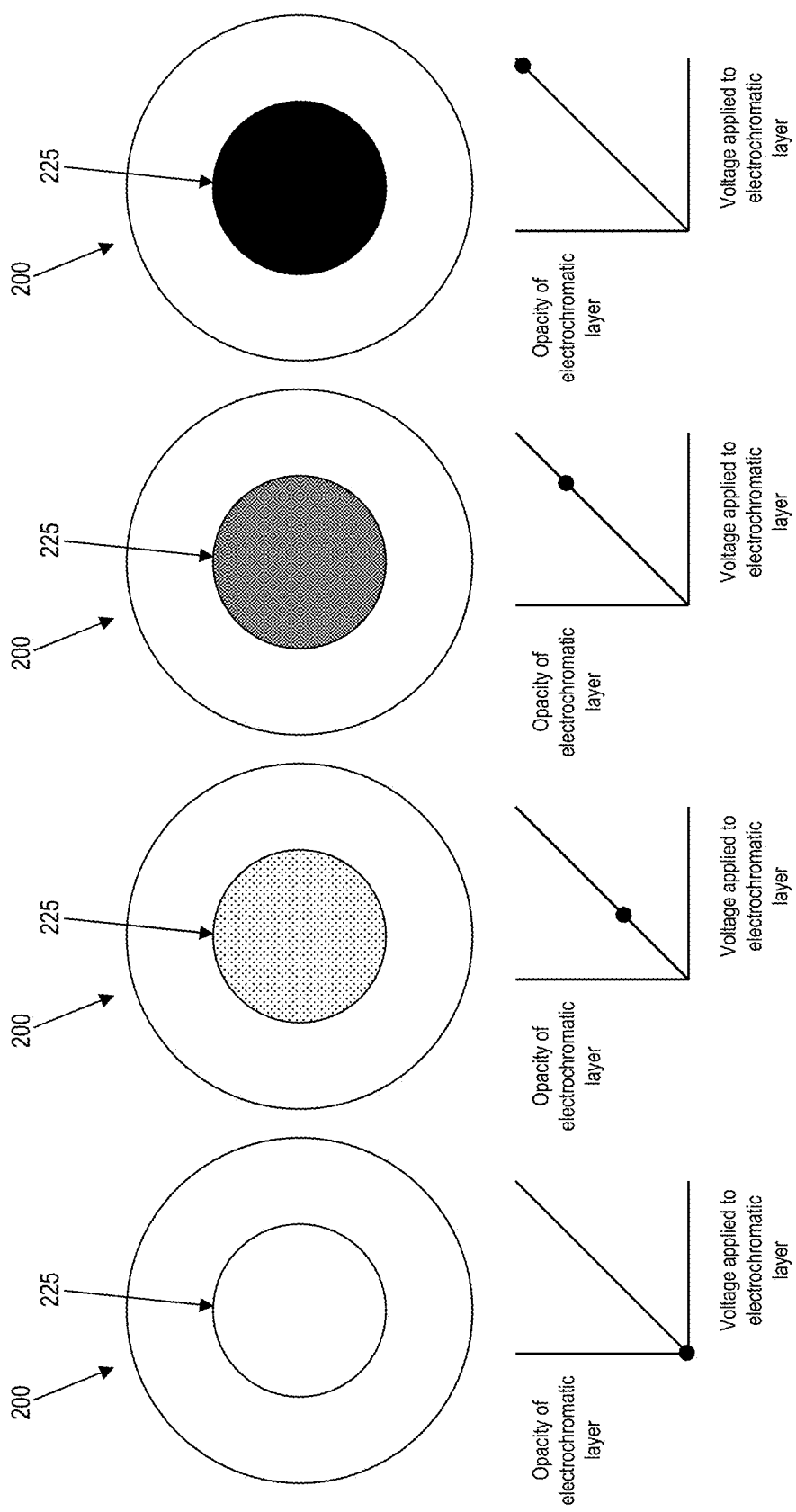
FIGS. 3A-D show an exemplary operation of a lens in accordance with aspects of the invention.

FIGS. 3A-D show an exemplary operation of the smart contact lens 200 in accordance with aspects of the invention. As described herein, the control circuit 240 adjusts the transmittance of the electrochromic layer 225 by applying a voltage to the electrochromic layer 225 via the anterior conductive electrode 215 and the posterior conductive electrode 220. As used herein, transmittance is a property of a material that described how much visible light passes through the material, and can range from 100% transmittance (e.g., transparent) to 0% transmittance (e.g., opaque). As shown in FIG. 3A, a first voltage applied to the electrochromic layer 225 causes the electrochromic layer 225 to have a first transmittance. As shown in FIG. 3B, a second voltage applied to the electrochromic layer 225 causes the electrochromic layer 225 to have a second transmittance. As shown in FIG. 3C, a third voltage applied to the electrochromic layer 225 causes the electrochromic layer 225 to have a third transmittance. As shown in FIG. 3D, a fourth voltage applied to the electrochromic layer 225 causes the electrochromic layer 225 to have a fourth transmittance. In this manner the control circuit 240 selectively controls the transmittance of the electrochromic layer 225 by adjusting an amount of voltage that is applied to the electrochromic layer 225. Aspects of the invention are no limited to the four discrete voltage and transmittance pairs shown in FIGS. 3A-D, and any number of different voltage levels may be used by the control circuit 240 to provide a corresponding number of different transmittance levels in the electrochromic layer 225.

Figure 4:
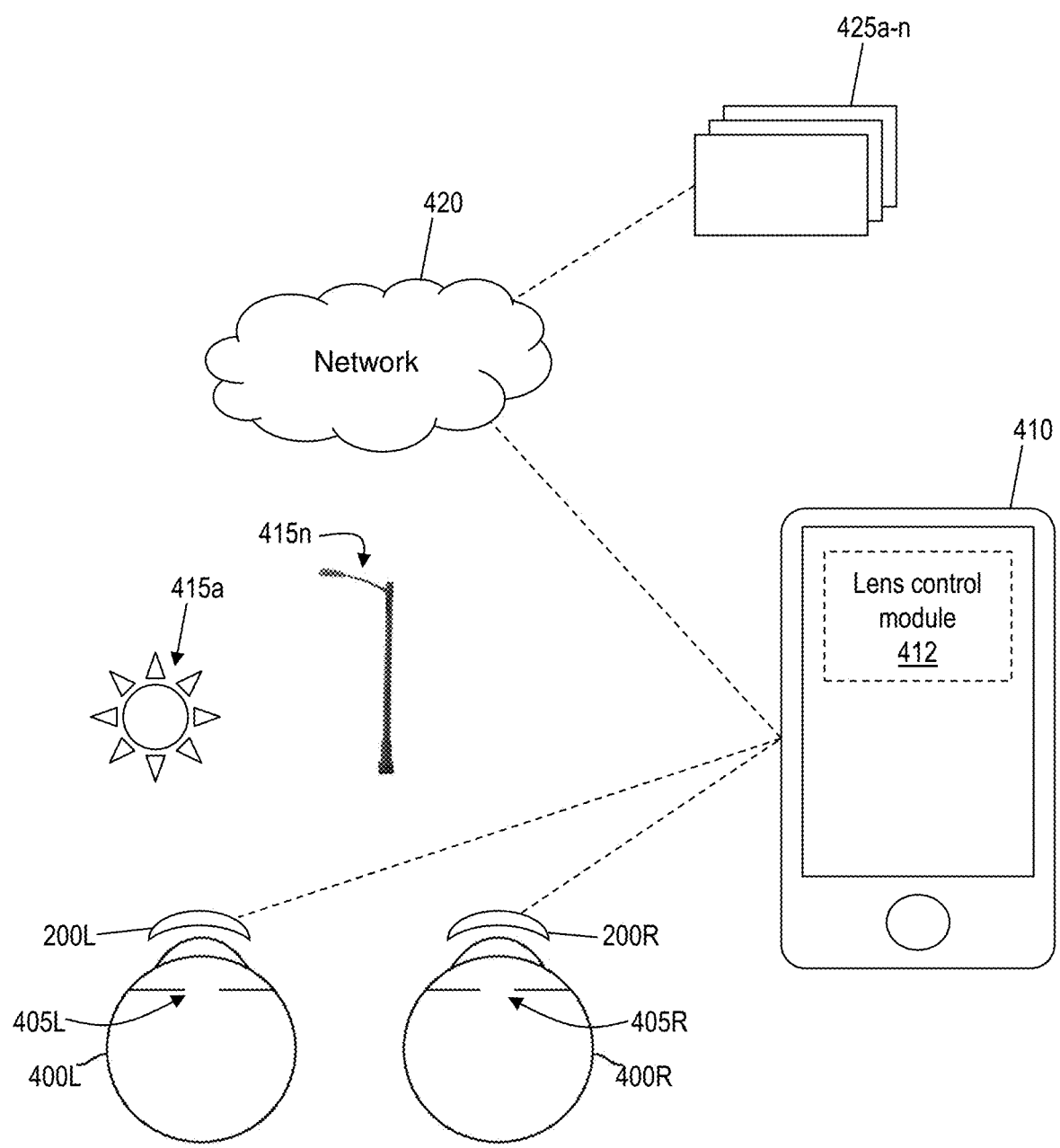
FIG. 4 shows a block diagram of an exemplary environment in accordance with aspects of the invention.

FIG. 4 shows a block diagram of an exemplary environment in accordance with aspects of the invention. In embodiments, the environment includes a lens 200L on a left eye 400L of a user and a lens 200R on a right eye 400R of the user. Each lens 200L, 200R is an instance of lens 200 described with respect to FIGS. 2 and 3, and may be worn on the outer surface of the respective eyes 400L, 400R in the traditional manner of contact lenses. In accordance with aspects of the invention, the environment also includes: a user device 410; one or more light sources 415a-n, a network 420, and one or more light sensors 425a-n.

The network 420 is any suitable combination of communication networks. For example, the network 420 may comprise one or more of a LAN, WAN, and the Internet.

The user device 410 is a computing device that comprises one or more elements of computer system 12 of FIG. 1. In one example, the user device 410 is a smartphone or tablet computer that is carried by the user that is wearing the lenses 200L, 200R. In embodiments, the user device 410 comprises a lens control module 412, which comprises one or more program modules such as program module 42 described with respect to FIG. 1. The user device 410 may include additional or fewer modules than those shown in FIG. 4. In embodiments, separate modules may be integrated into a single module. Additionally, or alternatively, a single module may be implemented as multiple modules. Moreover, the quantity of devices and/or networks in the environment is not limited to what is shown in FIG. 4. In practice, the environment may include additional devices and/or networks; fewer devices and/or networks; different devices and/or networks; or differently arranged devices and/or networks than illustrated in FIG. 4.

According to aspects of the invention, each lens 200L, 200R communicates wirelessly with the user device 410 using wireless protocol, such as Bluetooth, near field communication (NFC), etc. In embodiments, the wireless communication includes each lens 200L, 200R transmitting data collected by its respective photodiode sensor 270 and image sensor 275 to the user device 410 in real time. In embodiments, the wireless communication includes the user device 410 transmitting respective control signals to each lens 200L, 200R, the control signals being based on the data obtained by the photodiode sensor 270 and the image sensor 275 and being configured to adjust the transmittance of the respective electrochromic layer 225 in each lens. In this manner, the user device 410 receives real time data from each lens 200L, 200R and, in response, provides control signals to each lens 200L, 200R to control the adjustable transmittance of each lens 200L, 200R.

In embodiments, the wireless transmission from each lens 200L, 200R to the user device 410, and from the user device 410 to each lens 200L, 200R is made via the control circuit 240 of each lens 200L, 200R. For example, the control circuit 240 of a lens (e.g., lens 200L) may receive data from each of the photodiode sensor 270 and image sensor 275 of the lens, and transmit this data to the user device 410. The control circuit 240 of the same lens (e.g., lens 200L) may also receive control signals from the user device 410 and use these control signals to adjust the electrochromic layer 225 in this lens, e.g., by adjusting the voltage applied to the electrochromic layer 225 as described with respect to FIGS. 2 and 3A-D.

With continued reference to FIG. 4, in embodiments, the photodiode sensor 270 in each lens 200L, 200R is configured to detect an amount of ambient light that is incident on the lens (referred to herein as an incident light level), and to output data that defines this detected incident light level. The light may be from any number of light sources 415a-n, including the sun, street lights, headlights of oncoming vehicles, etc. In embodiments, each lens 200L, 200R transmits the data of its photodiode sensor 270 to the user device 410.

Also, in embodiments, the image sensor 275 in each lens 200L, 200R is configured to obtain image data of the pupil 405L, 405R in each eye 400L, 400R (referred to herein as pupil image data), and to output the image data of the pupil. In accordance with aspects of the invention, each lens 200L, 200R transmits the data of its image sensor 275 to the user device 410. In embodiments, for a respective lens (e.g., 200L) and eye (e.g., 400L), the lens control module 412 determines a size of the pupil (e.g., 405L) based on the pupil image data, e.g., using image processing techniques such as edge detection. In embodiments, the lens control module 412 determines a rate of change of the size of the pupil, e.g., by comparing the determined size of the pupil at different times. In embodiments, the lens control module 412 correlates the determined size of the pupil to the incident light level based on the time that the lens control module 412 receives the incident light level data from the photodiode sensor 270 and the time the lens control module 412 receives the pupil image data from the image sensor 275. In embodiments, the lens control module 412 correlates the rate of change of the size of the pupil to the incident light level based on the time that the lens control module 412 receives the incident light level data from the photodiode sensor 270 and the time the lens control module 412 receives the pupil image data from the image sensor 275.

In further embodiments, the lens control module 412 is configured to determine a blink rate of the eye (e.g., 400L) based on data from one or both of the photodiode sensor 270 and the image sensor 275. For example, the amount of ambient light detected by the photodiode sensor 270 is temporarily reduced to zero for a very short duration of time each time the user blinks. In embodiments, the lens control module 412 is configured to detect these data points as blinks of the eye of the user. In this embodiment, the lens control module 412 is also configured to determine a historic average blink rate for the user by averaging the number of detected blinks per unit time over many such data points.

In embodiments, the lens control module 412 collects and analyzes plural historic data points for a particular user, each data point including an incident light level (from the photodiode sensor 270 data) and a corresponding determined size of the pupil (from the image sensor 275 data). Based on this analysis, the lens control module 412 determines different respective average pupil sizes for this user for different respective incident light levels. The determined average pupil size for a user for a particular incident light level is referred to as a historic pupil size for this user for this incident light level. In embodiments, the lens control module 412 also determines a smallest historic pupil size for this user based on a smallest one of plural different historic pupil sizes for the user. In embodiments, the lens control module 412 determines these values independently for each different eye 400L, 400R of the use, since the different eyes may have different characteristics.

In accordance with aspects of the invention, the lens control module 412 controls the transmittance of the electrochromic layer 225 in one or more of the lenses 200L, 200R based on one or more of: the incident light level data from the photodiode sensor 270; the pupil image data from the image sensor 275a; and a historic pupil size for this user.

In one embodiment, the lens control module 412 adjusts the transmittance of the electrochromic layer 225 based on a determination that (i) the current pupil size is not equal to a historic pupil size for this user for this incident light level and (ii) the pupil size is currently changing (e.g., based on the rate of change of the size of the pupil). In this example, based on determining satisfaction of these two conditions, the lens control module 412 deems that the user's eye is not reacting sufficiently fast to the incident light level, and in response the lens control module 412 adjusts the transmittance of the electrochromic layer 225 to reduce its level of transmittance, i.e., to block more ambient light from passing through the smart contact lens 200 and impacting the eye that is having difficulty adjusting to the incident light level. In this manner, when the user experiences an abrupt change in the incident light level that strains the user's eye, the lens control module 412 detects this condition and adjusts the transmittance of the electrochromic layer 225 to block a portion of the incident light to reduce the strain on the user's eye.

In another embodiment, the lens control module 412 adjusts the transmittance of the electrochromic layer 225 based on a determination that (i) the current pupil size is the smallest historic pupil size and (ii) the user is blinking excessively (e.g., at a rate higher than the historic average blink rate for this user). In this example, based on determining satisfaction of these two conditions, the lens control module 412 deems that the user is experiencing eye strain because the user is blinking the eye at a higher than normal rate concurrently with the eye having adjusted the pupil to the maximum extent (i.e., the smallest historic pupil size for this user). As a result, the lens control module 412 adjusts the transmittance of the electrochromic layer 225 to reduce its level of transmittance, i.e., to block more ambient light from passing through the smart contact lens 200 and impacting the eye that is having difficulty. In this manner, when the user experiences an incident light level that strains the user's eye due to being outside this user's range of pupillary control, the lens control module 412 detects this condition and adjusts the transmittance of the electrochromic layer 225 to block a portion of the incident light to reduce the strain on the user's eye.

With continued reference to FIG. 4, the previously described examples include the lens control module 412 adjusting the electrochromic layer 225 in a reactive manner. Additional aspects of the invention involve the lens control module 412 adjusting the electrochromic layer 225 in a proactive manner based on data obtained from one or more light sensors 425a-n that are external to the user wearing the lenses 200L, 200R.

According to aspects of the invention, the one or more light sensors 425a-n are sensors that detect levels of light at various geographic locations, and that publish data indicating the detected light levels to the network 420. For example, the one or more light sensors 425a-n may comprise sensors installed along roads, sidewalks, and in and around entrances of buildings, e.g., at locations where fast transitions of ambient light level can occur and affect users. Each of the one or more light sensors 425a-n may comprise any suitable conventional or later developed sensor that detects a level of visible light. In embodiments, each of the one or more light sensors 425a-n comprises an Internet of Things (IoT) device that detects the light level at its location and publishes this light data to the network, the light data for a particular one of the sensors including: (i) the detected light level, (ii) a location (e.g., GPS location) of the sensor, and (iii) a timestamp associated with the detected light level. In this embodiment, the lens control module 412 can obtain light data published the sensors 425a-n via the network 420.

In a particular exemplary implementation, the lens control module 412 utilizes data from one or more of the sensors 425a-n to proactively control the transmittance of the electrochromic layer 225 in one or more of the lenses 200L, 200R. In embodiments, the lens control module 412 determines a predicted path of travel of the user, identifies one or more of the sensors 425a-n along the predicted path of travel of the user, and analyzes the light data from each of the identified sensors 425a-n to determine locations of abrupt changes in light levels along the predicted path of travel of the user. In this embodiments, based on determining a location of an abrupt light level change along the predicted path of travel of the user, the lens control module 412 adjusts the transmittance of the electrochromic layer 225 in one or more of the lenses 200L, 200R as the user is approaching or arriving at the determined location of the abrupt light level change. In this manner, the lens control module 412 proactively adjusts the transmittance of the electrochromic layer 225 at a time immediately prior to, or coincident with, a determined location of an abrupt light level change, so as to reduce strain on the eye of the user that might otherwise result from the abrupt light level change.

As used herein, an abrupt light level change refers to a change in light levels between two locations, where the amount of the change exceeds a predefined threshold value. In one example, the two locations include a first location corresponding to the current location of the user wearing the lenses 200L, 200R, and a second location corresponding to a location of one of the identified sensors 425a-n along the determined path of travel of the user. In a particular implementation of this example, the second location is the next identified sensor along the determined path of travel of the user. In another example, the two locations include different locations of two of the identified sensors 425a-n along the determined path of travel of the user. Still referring to the abrupt light level change, in one example the predefined threshold value is a default value programmed into the lens control module 412. In another example, the lens control module 412 determines the predefined threshold value based on historic data associated with the user wearing the lenses 200L, 200R. For example, the lens control module 412 may be configured to analyze historic data of this use to determine when different amounts of change of incident light level (e.g., based on data from the photodiode sensor 270) results in detected eye strain (e.g., where eye strain is detected in the manner already described herein).

In embodiments, the lens control module 412 determines the predicted path of travel of the user based on GPS data of the user device 410. In one example, if the user has programmed a route into a mapping application of the user device 412, the lens control module 412 determines the predicted path of travel based on the route. In another example, the lens control module 412 determines a direction of travel of the user by analyzing plural successive GPS locations of the user device 410, compares the current GPS location of the user device 410 and the determined direction of travel to map data, and determines the predicted path of travel by selecting a map feature (e.g., roads, sidewalks, buildings, etc.) that most closely coincides with the current GPS location of the user device 410 and the determined direction of travel.

In embodiments, based on determining the predicted path of travel of the user, the lens control module 412 identifies one or more of the sensors 425a along the predicted path of travel by comparing the location data of the sensors 425a-n to location data defining the predicted path of travel. In this embodiment, the lens control module 412 compares the light data of the identified sensors 425a-n along the predicted path of travel to determine whether the user wearing the lenses 200L, 200R will experience an abrupt light level change along the predicted path of travel. In this implementation, based on determining an abrupt light level change along the predicted path of travel, the lens control module 412 proactively determines the location of the abrupt light level change (e.g., based on the light data of the sensors 425a-n), and adjusts the transmittance of the electrochromic layer 225 at a time when the user's current location is immediately prior to, or coincident with, the determined location of the abrupt light level change. In this manner, the system reduces strain on the eye of the user that might otherwise result from the abrupt light level change.

As described thus far, aspects of the invention include a smart contact lens 200 that includes a flexible display layer 280 and an adjustable electrochromic layer 225. In embodiments, the lens includes a micro battery (e.g., power supply 235) and a photodiode sensor 270 that can generate power from visible light and recharge the micro battery. In embodiments, a pupil portion of the smart contact lens 200 includes the electrochromic layer 225, so that when a level of transmittance of this layer is changed, it will control the brightness of light falling on the retina of the user. As described herein, the photodiode sensor 270 of the smart contact lens 200 detects a level of brightness in the surrounding. In embodiments, the smart contact lens is 200 has an image sensor 275 (e.g., a camera), the data of which can be used to track the pupillary light reflex of the user. For example, the image sensor 275 may be configured to scan the internal eye structure, such that its data may be used to track the pupillary light reflex of the user. In embodiments, the smart contact lens 200 tracks the user's eye movement with respect to brightness of the eye, closing of eye, etc.

In implementations, and as described herein, the smart contact lens 200 continuously communicates with the user device 410 in real time, such that the lens control module 412 stored on the mobile device analyzes data obtained by the smart contact lens 200. Based on analyzing the data, the lens control module 412 identifies abnormal pupillary light reflex of the user and, accordingly be, determines if the user is having any problem with their pupillary light reflex (e.g., by comparing the current pupillary light reflex to a historic normal pupillary light reflex for this user).

In additional implementations, and as described herein, the mobile device 410 communicates with surrounding IoT devices (e.g., sensors 425a-n) to track levels of brightness distribution in a surrounding. In these embodiments, the mobile device 410 uses a movement sensor (e.g., GPS) to track a movement direction and speed of movement of the user. In these embodiments, based on the distribution of light in the surrounding and the user's movement direction, the mobile device 410 determines if the user is moving from bright surrounding to less or dark surrounding or vice versa (e.g., an abrupt light level change). In these embodiments, based on the identified speed of movement of the user, the mobile device 410 determines how long the user will take to move from one level of brightness in the surrounding to another level of brightness in the surrounding. In these embodiments, the mobile device 410 calculates how the transmittance level of the electrochromic layer 225 should be adjusted in order to the control the brightness of the light falls on the retina of the user wearing the smart contact lens 200. In particular embodiments, the lens control module 412 controls the rate of change in the transmittance level of the electrochromic layer 225 based on a rate of adaptation required by this user while moving one level of brightness to another level of brightness. In embodiments, the rate of change in the transmittance level of the electrochromic layer 225 is calculated based on historical data of this same user about their pupillary light reflex (e.g., based on data from the photodiode sensor 270 and the image sensor 275). In embodiments, the battery of the smart contact lens 200 provides appropriate power support to change the transmittance level of the electrochromic layer 225.

With continued reference to FIG. 4, in accordance with further aspects of the invention, the module 412 adjusts the transmittance of the electrochromic layer 225 to be opaque while concurrently controlling the display layer 280 to display virtual reality (VR) content to a user wearing the smart contact lens 200.

In embodiments, based on VR content navigation, the pupil area of smart content lens 200 is adjusted to a completely opaque area to restrict external light to fall on the retina. In this manner, the user will lose visual contact from the physical world and, accordingly, VR content can be projected in the retina from the smart contact lens via the display layer 280.

In embodiments, the user device 410 controls each of the two lenses 200L and 200R independently from one another, e.g., by sending different control signals to each of the lenses 200L, 200R. In some embodiments, each lens 200L, 200R is paired to the user device 410 independently of the other lens, and each lens 200L, 200R has a unique indetifier that is used in communications with the user device 410. In this manner, the user device 410 sends appropriate visual content to each of the lenses 200L, 200R. When the lenses 200L, 200R display their respective visual content simultaneously, the resulting 3D virtual reality content is constructed in the brain of the user based on the visual content.

In embodiments, that photoelectric diode (photodiode sensor 270) of the smart contact lens 200 generates power for displaying the VR content. In some instances, the system enables external light or light is focused around the eye area programmatically.

In embodiments, the smart contact lens 200 includes a piezoelectric crystal, which generates power from eye blink based mechanical work. In this manner, when power is required (e.g., the battery charge is low), the smart contact lens 200 displays a visual indication to the user to notify the user to blink more frequently, to generate power. A mixed reality system can be used for the notification.

In embodiments, the user controls VR aspects of the lens utilizing predefined signals (e.g., voice, gesture, biometric, etc.). In this manner, the user can provide a signal to the system that causes the system to: shut down the VR content; and adjust the transmittance of the lens to be transparent again, so that the user can see through the lens.

Figure 5:
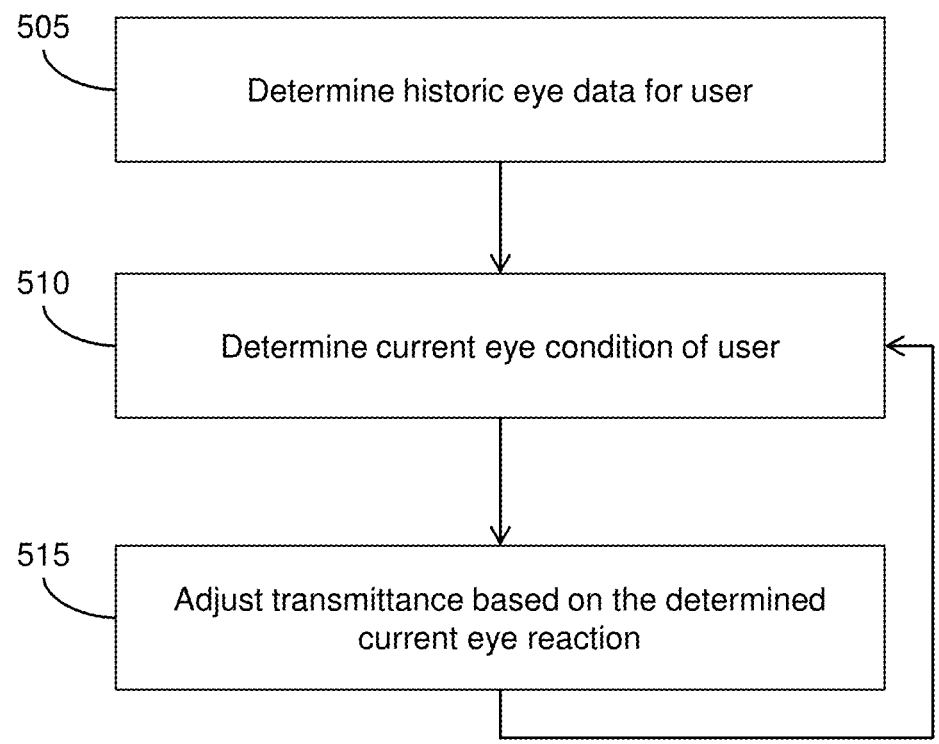
FIG. 5 shows a flowchart of an exemplary method in accordance with aspects of the invention.

FIG. 5 shows a flowchart of an exemplary method in accordance with aspects of the present invention. Steps of the method may be carried out in the environments of FIGS. 2 and 4 and are described with reference to elements depicted in FIGS. 2-4.

At step 505, the system determines historic eye data for a user. In embodiments, and as described with respect to FIG. 4, the user wears lenses 200L, 200R and pairs the lenses with the user device 410 to establish wireless communication between the lenses and user device. In embodiments, and as described with respect to FIG. 4, the photodiode sensor 270 obtains incident light level data and the image sensor 275 of obtains pupil image data over plural data points while the user wears the lenses 200L, 200R. In aspects, and as described with respect to FIG. 4, the lenses 200L, 200R transmit this data to user device 410, and the lens control module 412 analyzes the data to determine for each eye and its associated lens: size of the pupil for incident light level at each data point; rate of change of the size of the pupil for incident light level at each data point; historic pupil sizes for different respective incident light levels over plural data points; smallest historic pupil size over plural data points; blink rate at each data point; and historic average blink rate over plural data points. In embodiments, the lens control module 412 stores the data in memory (e.g., data storage) of the user device 410.

At step 510, the system determines a current eye condition of the user (e.g., the user for which historic eye data was determined at step 505). In embodiments, and as described with respect to FIG. 4, the photodiode sensor 270 obtains current incident light level data and the image sensor 275 of obtains current pupil image data while the user wears the lenses 200L, 200R, and the lenses transmit the current data to the lens control module 412 in real time. In embodiments, and as described with respect to FIG. 4, the lens control module 412 determines a current eye condition of the user based on the current data obtained at step 510 and the determined historic eye data obtained at step 505. In embodiments, the lens control module 412 determines in real time: a current pupil size of the eye of the user based on the current pupil image data; a current rate of change of the size of the pupil based on the current pupil image data; and a current blink rate based on the current pupil image data.

In the context of step 510, the terms current data and current pupil image data encompass one or more data points from the lens within a predefined amount of time relative to the current time. For example, the current pupil size of the eye of the user may be determined based on a single most recent data point of the pupil image data received from the image sensor 275. As another example, the current rate of change of the size of the pupil may be determined based on a predefined number (e.g., 3) of most recent data points of the pupil image data received from the image sensor 275. As another example, the current blink rate may be determined based on a predefined number (e.g., 3) of most recent data points of the pupil image data received from the image sensor 275.

Still referring to step 510, in one embodiment, the lens control module 412 determines the eye condition comprises insufficient pupillary reaction to the current incident light level. In this embodiment, the lens control module 412 makes this determination based on determining that the following conditions are satisfied: (i) the current pupil size is not equal to a historic pupil size for this user for this incident light level and (ii) the pupil size is currently changing (e.g., based on the current rate of change of the size of the pupil as determined in this step). As such, in this embodiment, step 510 includes the lens control module 412 comparing the current pupil size (e.g., determined at step 510) to the historic pupil size for this user for the current incident light level (e.g., the historic pupil size for different incident light levels having been determined at step 505). In response to determining that both conditions are satisfied, the lens control module 412 adjusts the transmittance of the electrochromic layer 225 of the lens to block more light from entering the user's eye, as described herein at step 515.

Still referring to step 510, in another embodiment, the lens control module 412 determines the eye condition comprises the eye strain at the current incident light level. In this embodiment, the lens control module 412 makes this determination based on determining that the following conditions are satisfied: (i) the current pupil size is the smallest historic pupil size and (ii) the user is blinking excessively (e.g., at a rate higher than the historic average blink rate for this user). As such, in this embodiment, step 510 includes the lens control module 412 comparing the current pupil size (e.g., determined at step 510) to the smallest historic pupil size (e.g., the smallest historic pupil size for tis user having been determined at step 505). In this embodiment, step 510 also includes the lens control module 412 comparing the current blink rate (e.g., determined at step 510) to the historic average blink rate for this user (e.g., the historic average blink rate for this user having been determined at step 505). In response to determining that both conditions are satisfied, the lens control module 412 adjusts the transmittance of the electrochromic layer 225 of the lens to block more light from entering the user's eye, as described herein at step 515.

At step 515, the system adjusts the transmittance of the lens based on the determined current eye condition (from step 510). In embodiments, and as described with respect to FIG. 4, based on determining at step 510 that the user eye condition comprises insufficiently fast pupillary reaction to the current incident light level or eye strain, the lens control module 412 adjusts the transmittance of the electrochromic layer 225 of the lens to block more light from entering the user's eye. In embodiments, and as described with respect to FIG. 4, the lens control module 412 causes the user device 410 to transmit a control signal to the lens (e.g., 200L, 200R), where the control signal causes the control circuit 240 of the lens to adjust the voltage applied to the electrochromic layer 225 of the lens in order to reduce the transmittance of the electrochromic layer 225. This real time reduction in the transmittance of the electrochromic layer 225 of the lens reduces the amount of ambient light that enters the user's eye through the lens, and thus can help alleviate ill effects of the current eye condition.

As described herein, steps 510 and 515 may be performed in real time and may be repeated over time as the user encounters different ambient light levels. In this manner, the system is configured to repeatedly adjust the transmittance of the electrochromic layer 225, as necessary, based on the new data obtained at each instance of step 510. Also, as described herein, steps 510 and 515 may be performed concurrently and independently for each lens 200L and 200R worn by a single user. For example, the different eyes of a same user may have different characteristics and different historic eye data, and the system may control the respective electrochromic layer 225 in each of the two lenses based on data for the eye associated with the lens.

Figure 6:
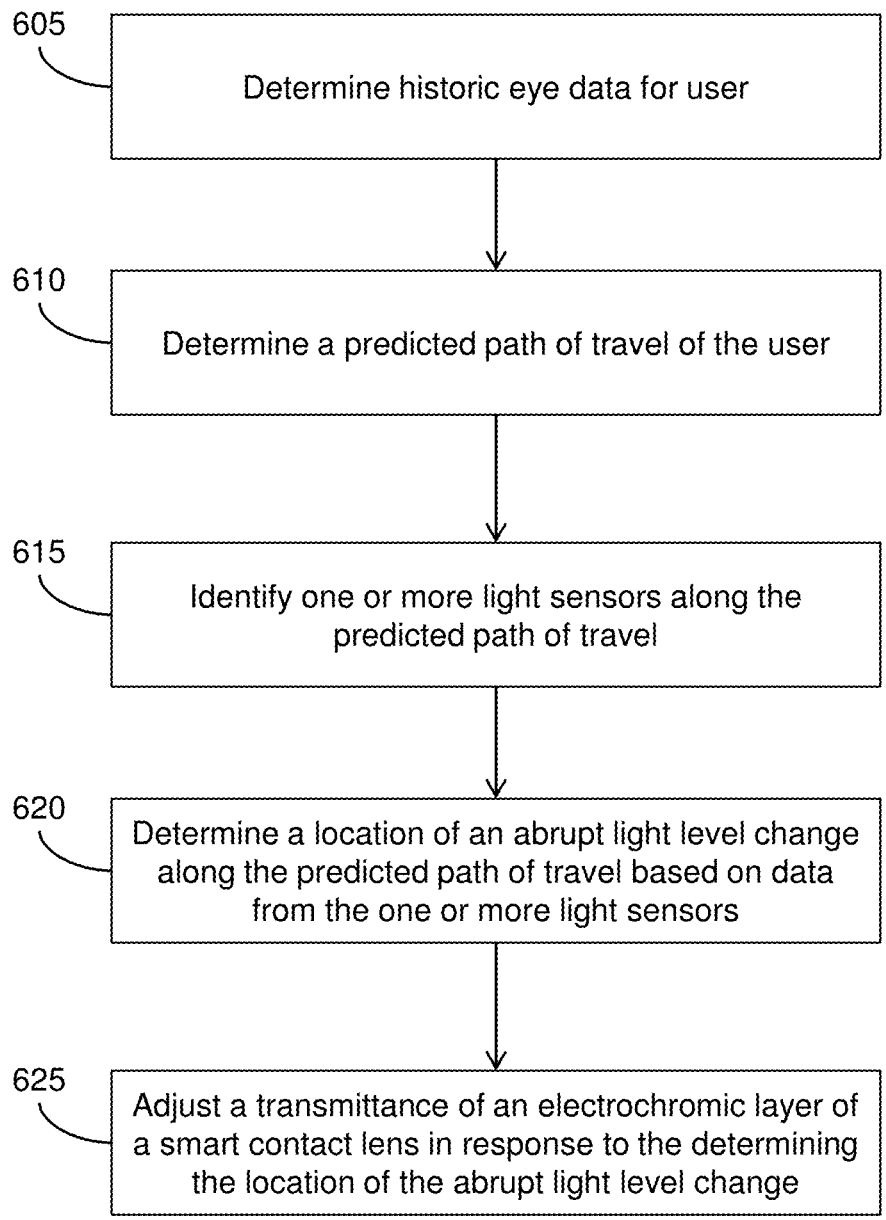
FIG. 6 shows a flowchart of another exemplary method in accordance with aspects of the invention.

FIG. 6 shows a flowchart of another exemplary method in accordance with aspects of the present invention. Steps of the method may be carried out in the environments of FIGS. 2 and 4 and are described with reference to elements depicted in FIGS. 2-4.

At step 605, the system determines historic eye data for a user. In embodiments, step 605 is performed in the same manner as step 505.

At step 610, the system determines a predicted path of travel for the user wearing the smart contact lens 200. In embodiments, and as described with respect to FIG. 4, the lens control module 412 determines the predicted path of travel of the user based on GPS data of the user device 410.

At step 615, the system identifies one or more light sensors along the predicted path of travel. In embodiments, and as described with respect to FIG. 4, the lens control module 412 identifies one or more of the sensors 425a along the predicted path of travel (from step 610) by comparing the location data of the sensors 425a-n to location data defining the predicted path of travel.

At step 620, the system determines a location of an abrupt light level change along the predicted path of travel based on data from the one or more light sensors. In embodiments, and as described with respect to FIG. 4, the lens control module 412 compares the light data of the identified sensors 425a-n along the predicted path of travel to determine whether the user wearing the lens will experience an abrupt light level change along the predicted path of travel.

At step 625, the system adjusts a transmittance of an electrochromic layer of the smart contact lens in response to the determining the location of the abrupt light level change. In embodiments, and as described with respect to FIG. 4, the lens control module 412 proactively determines the location of the abrupt light level change (e.g., based on the light data of the sensors 425a-n), and adjusts the transmittance of the electrochromic layer 225 at a time when the user's current location is immediately prior to, or coincident with, the determined location of the abrupt light level change.

Figure 7:
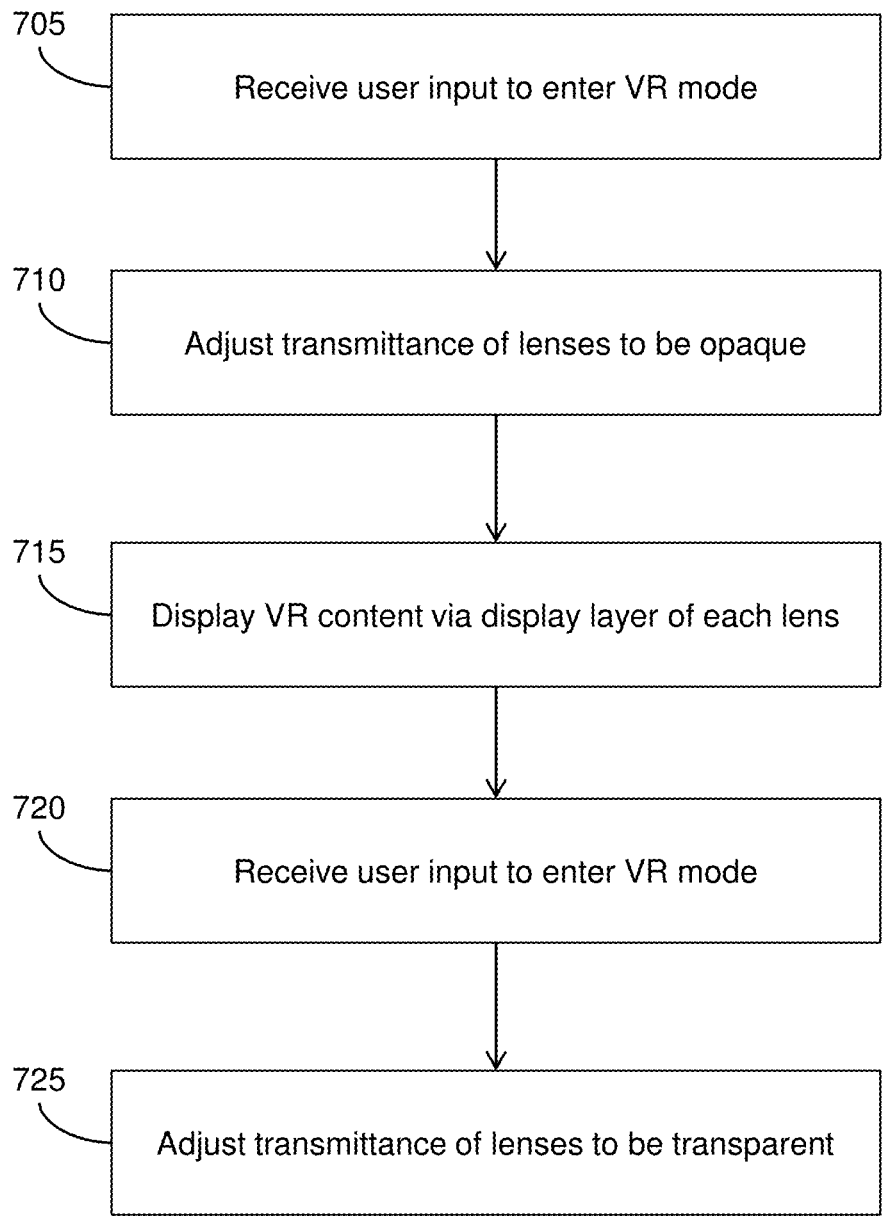
FIG. 7 shows a flowchart of another exemplary method in accordance with aspects of the invention.

FIG. 7 shows a flowchart of another exemplary method in accordance with aspects of the present invention. Steps of the method may be carried out in the environments of FIGS. 2 and 4 and are described with reference to elements depicted in FIGS. 2-4.

At step 705, the system receives user input to enter VR mode. In embodiments, and as described with respect to FIG. 4, the user provides a predefined input to the user device 410 by, for example, voice command, physical gesture, or touchscreen input, where the user device 410 is configured to interpret the predefined input with entering VR mode. In embodiments, the input can be a predefined sequence of blinks by one or both eyes 400L, 400R.

At step 710, the system adjusts transmittance of lenses to be opaque. In embodiments, and as described with respect to FIG. 4, in response to the user input at step 705, the module 412 sends controls signals to the lenses 200L, 200R to adjust the transmittance of electrochromic layer 225 to a first predefined value. In embodiments, the first predefined value is a transmittance value such that the electrochromic layer 225 is essentially opaque to the user wearing the lens. As used herein, essentially opaque means that the user cannot discern visible light coming in through the electrochromic layer 225. In embodiments, essentially opaque can include transmittance values of 0%, as well as transmittance values close to 0% (e.g., 1%, 2%, etc.) where the user cannot discern visible light coming in through the electrochromic layer 225.

At step 715, the system displays VR content via the display layer of each lens. In embodiments, and as described with respect to FIG. 4, in response to the user input at step 705, the module 412 sends controls signals to the lenses 200L, 200R to cause visual content to be displayed on the display layer 280. In embodiments, and as described herein, the visual content for each lens 200L, 200R is different, such that when the different content is simultaneously displayed by each lens 200L, 200R, the user's brain combines the content into the intended VR content.

At step 720, the system receives user input to exit VR mode. In embodiments, and as described with respect to FIG. 4, the user provides a predefined input to the user device 410 by, for example, voice command, physical gesture, or touchscreen input, where the user device 410 is configured to interpret the predefined input with exiting VR mode. In embodiments, the input can be a predefined sequence of blinks by one or both eyes 400L, 400R.

At step 725, the system adjusts transmittance of lenses to be transparent. In embodiments, and as described with respect to FIG. 4, in response to the user input at step 720, the module 412 sends controls signals to the lenses 200L, 200R to adjust the transmittance of electrochromic layer 225 to a second predefined value. In embodiments, the second predefined value is a transmittance value such that the electrochromic layer 225 is essentially transparent to the user wearing the lens. As used herein, essentially transparent means that the user can discern visible light coming in through the electrochromic layer 225. Step 725 may also include the system discontinuing showing content on the display layer 280. After step 725, the system may adjust the transmittance of the electrochromic layer 225 in accordance with the methods of one of FIGS. 5 and 6.

As described herein, a system may include the user device 410 combined with one lens 200 or two lenses 200L, 200R. In embodiments, such a system may be configured to perform all three methods. For example, the system may perform the method of FIG. 5 at first time. The same system worn by the same user may perform the method of FIG. 6 a second time different than the first time. The same system worn by the same user may perform the method of FIG. 7 a third time different than the first time and the second time.

In embodiments, a service provider could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/or the service provider can receive payment from the sale of advertising content to one or more third parties.

In still additional embodiments, the invention provides a computer-implemented method, via a network. In this case, a computer infrastructure, such as computer system 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
   determining, by a computing device, historic eye data of a user;
   determining, by the computing device, a current eye condition of the user based on: current data from a photodiode sensor of a smart contact lens worn by the user; current data from an image sensor of the smart contact lens worn by the user; and the historic eye data of the user; and
   adjusting, by the computing device, a transmittance of the smart contact lens worn by the user based on the determined current eye condition.

2. The method of claim 1, wherein the adjusting the transmittance of the smart contact lens comprises applying a voltage to an electrochromic layer included in the smart contact lens.

3. The method of claim 1, wherein:
the computing device comprises a user device that communicates wirelessly with the smart contact lens; and
the adjusting the transmittance of the smart contact lens comprises the user device sending a control signal to the smart contact lens, the control signal causing a control circuit of the smart contact lens to apply a voltage to an electrochromic layer included in the smart contact lens.

4. The method of claim 1, wherein the current eye condition of the user comprises insufficient pupillary reaction determined based on: a current pupil size of the user; a historic pupil size for the user for a current incident light level; and a current rate of change of the pupil size of the user.

5. The method of claim 1, wherein the current eye condition of the user comprises eye strain at a current incident light level determined based on: a current pupil size of the user; a smallest historic pupil size of the user; a current blink rate of the user; and a historic average blink rate of the user.

6. The method of claim 1, wherein the historic eye data of the user comprises:
historic pupil sizes for different respective incident light levels;
smallest historic pupil size; and
historic average blink rate over plural data points.

7. The method of claim 1, wherein:
the smart contact lens comprises one of two different smart contact lenses worn by the user; and
the computing device performs the determining the historic eye data, the determining the current eye condition, and the adjusting the transmittance separately for the two different smart contact lenses worn by the user.

8. The method of claim 1, wherein the image sensor of the smart contact lens captures image data on an interior of the user's eye when the user is wearing the smart contact lens.

9. The method of claim 1, further comprising:
obtaining data from the one or more light sensors that are external to a user wearing the smart contact lens; and
adjusting the transmittance of the smart contact lens based on the data from the one or more light sensors,
wherein the one or more light sensors comprise plural Internet of Things (IoT) sensors at plural different locations; and
each of the IoT sensors is configured to publish light data to a network, the light data including: a light level detected by the one of the IoT sensors; a location of the one of the IoT sensors; and a timestamp associated with the detected light level.

10. A computer program product comprising one or more computer readable storage media having program instructions collectively stored on the one or more computer readable storage media, the program instructions executable to cause a computing device to:
adjust a transmittance of an electrochromic layer of a smart contact lens based on data from one or more light sensors that are external to a user wearing the smart contact lens,
wherein the computing device communicates wirelessly with the smart contact lens;
the computing device obtains the data from the one or more light sensors via a network;
the one or more light sensors comprise plural Internet of Things (IoT) sensors at plural different locations; and
each of the IoT sensors is configured to publish light data to the network, the light data including: a light level detected by the one of the IoT sensors; a location of the one of the IoT sensors; and a timestamp associated with the detected light level.

11. The computer program product of claim 10, wherein the program instructions are executable to cause the computing device to:
determine a predicted path of travel of the user wearing the smart contact lens; and
identify the one or more light sensors along the predicted path of travel.

12. The computer program product of claim 11, wherein the program instructions are executable to cause the computing device to:
determine a location of an abrupt light level change along the predicted path of travel based on data from the one or more light sensors; and
perform the adjusting the transmittance in response to the determining the location of the abrupt light level change.

13. The computer program product of claim 12, wherein the abrupt light level change comprises a change in light levels between two locations, where an amount of the change in light levels exceeds a predefined threshold value.

14. A system, comprising:
a smart contact lens comprising:
an electrochromic layer;
a display layer; and
a control circuit configured to adjust a transmittance of the electrochromic layer to a predefined value while concurrently controlling the display layer to display virtual reality content to a user wearing the smart contact lens.

15. The system of claim 14, wherein:
the smart contact lens comprises one of two smart contact lenses worn by the user;
each of the two smart contact lenses receives control signals from a user device, the control signals causing each of the each of the two smart contact lenses to display different respective portions of the virtual reality content.

16. The system of claim 14, wherein the predefined value of transmittance is substantially opaque.

17. The system of claim 14, wherein the display layer is between the electrochromic layer and the user's eye when the user is wearing the smart contact lens.

18. The system of claim 14, wherein the display layer comprises a microLED display.

19. The system of claim 14, wherein, after controlling the display layer to display the virtual reality content, the control circuit is configured to:
adjust the transmittance of the electrochromic layer so that the electrochromic layer is transparent; and
control the display layer to discontinue displaying any visual content to the user.

20. The system of claim 14, wherein the control circuit is configured to:
obtain data from the one or more light sensors that are external to a user wearing the smart contact lens; and
adjust the transmittance of the electrochromic layer based on the data from the one or more light sensors,
wherein the one or more light sensors comprise plural Internet of Things (IoT) sensors at plural different locations; and each of the IoT sensors is configured to publish light data to a network, the light data including: a light level detected by the one of the IoT sensors; a location of the one of the IoT sensors; and a timestamp associated with the detected light level.

* * * * *